US007345035B2

(12) United States Patent
Taber et al.

(10) Patent No.: US 7,345,035 B2
(45) Date of Patent: Mar. 18, 2008

(54) TREATMENT OF OSTEOPOROSIS AND AUTOIMMUNE DISEASE WITH ASTROGORGIADIOL

(75) Inventors: Douglass F. Taber, Newark, DE (US); Mary C. Farach-Carson, Hockessin, DE (US); Scott C. Malcolm, Hopkinton, MA (US); Yihuan Xu, Newark, DE (US)

(73) Assignee: University of Delaware, Newark, DE (US)

( * ) Notice: Subject to any disclaimer, the term of this patent is extended or adjusted under 35 U.S.C. 154(b) by 516 days.

(21) Appl. No.: 10/446,218

(22) Filed: May 28, 2003

(65) Prior Publication Data

US 2004/0242677 A1    Dec. 2, 2004

(51) Int. Cl.
 *A61K 31/56* (2006.01)
(52) U.S. Cl. ...................... 514/181; 514/182
(58) Field of Classification Search ........... 514/181, 514/182
 See application file for complete search history.

(56) References Cited

OTHER PUBLICATIONS

Fusetani et al., Tetrahedron Letters, 1989;39(50):7079-7082.*
Merck Index, 10th ed., 1983, monograph 212, pp. 34-35.*
Taber, D.F. et al., J. Org. Chem. 2001, 66, 944-953; "Synthesis of (-)-Astrogorgiadiol".
Taber, D.F. et al., J. Org. Chem. Jul. 12, 2002, 67, 4821-4827; "Synthesis of (-)-Calicoferol B" (published on Web Jun. 13, 2002).
Farach-Carson, M.C. et al., American Physiological Society,1993, 265, F705-F711; "22-Osacalcitrol: dissection of $1,25(OH)_2D_3$ receptor-mediated and $Ca^{2+}$ entry-stimulating pathways".
Fusetani et al., Tetrahedron Letters 1989, 30, 7079-7082, "Astrogorgiadiol and astrogorgin, inhibitors of cell division in fertilized starfish eggs, from a gorgonian", (Abstract).
Chabas D. et al., Science 2001, 294, 1731-1735, "The Influence of the Proinflammatory Cytokine, Osteopontin, on Autoimmune Demyelinating Disease".
Forton, et al., Human Mutation 2002, Mutation in Brief #496 Online, "An Osteopontin (SPP1) Polymorphism is Associated with Systemic Lupus Erythematosus".
Yoshitake, H. et al., Proc. Nat'l Acad. Sci. USA 1999, 96, 8156-8160, "Osteopontin-deficient mice are resistant to ovariectomy-induced bone resporption".

* cited by examiner

Primary Examiner—San-Ming Hui
(74) Attorney, Agent, or Firm—RatnerPrestia

(57) ABSTRACT

The invention provides methods of downregulating mRNA encoding osteopontin comprising administering to a cell or mammal an amount of astrogorgiadiol effective to downregulate production of mRNA encoding osteopontin. The invention also provides methods of treating osteoporosis and autoimmune disease comprising administering to a patient in need of such treatment a therapeutically effective amount of astrogorgiadiol. Pharmaceutical compositions comprising astrogorgiadiol and a pharmaceutically acceptable carrier or diluent are also provided.

11 Claims, 1 Drawing Sheet

TREATMENT OF OSTEOPOROSIS AND AUTOIMMUNE DISEASE WITH ASTROGORGIADIOL

REFERENCE TO U.S. GOVERNMENT SUPPORT

This invention was made in part with government support under a grant from the National Institutes of Health (grant number R01 DE 12641-01A1). The United States government has certain rights in the invention.

FIELD OF THE INVENTION

The invention relates to the field of treatments for osteoporosis and/or autoimmune diseases. More particularly the invention relates to downregulation of osteopontin by the vitamin D3 derivative astrogorgiadiol for treatment of osteoporosis and/or autoimmune disease.

BACKGROUND OF THE INVENTION

Ostepontin is one of the major noncollagenous bone matrix proteins produced by osteoblasts and osteoclasts. Substrate-bound osteopontin promotes attachment of osteoclasts, whereas soluble osteopontin can alter calcium levels in osteoclasts, suppress inducible nitric oxide synthase induction in kidney cells and macrophages and serve as a chemoattractant.

Increased production of osteopontin has been associated with osteoporosis and autoimmune diseases, including systemic lupus erythematosis and multiple sclerosis.

Multiple sclerosis (MS) affects approximately one million people worldwide with women twice as likely to have the disease. At present, multiple sclerosis is uncurable and the cause is unknown. In multiple sclerosis, inflammation of nerve tissue destroys the myelin covering of nerve cells axons, leaving areas of scar tissue. This patchy loss of myelin in the brain and spinal cord slows communication between nerve cells, leading to symptoms such as muscle spasms, weakness, sensory deficits and visual disturbances. Chabas et al., Science 294: 1731-1735 (2001) studied the influence of osteopontin on autoimmune demyelinating disease and found that osteopontin transcripts were increased in an experimental mouse model of multiple sclerosis, experimental autoimmune encephalomyelitis, and that osteopontin-deficient mice were resistant to progressive experimental autoimmune encephalomyelitis and had frequent remissions.

Humans with systemic lupus erythematosus overexpress osteopontin.

Osteoarthritis-affected cartilage exhibits enhanced expression of fibronectin and osteopontin. Yoshitake et al. Proc. Nat'l Acad. Sci. USA 96: 8156-8160 (1999) reported that osteopontin-deficient knockout mice are resistance to ovariectomy-induced bone resorption. Post menopausal osteoporosis is one of the most common diseases affecting aged women. Withdrawal of estrogen after menopause causes loss of bone mineral because of an increase in osteoclastic bone resorption. Supplementation with estrogen can reduce bone loss not only in humans but also in animal models.

Astrogorgiadiol (1) is a naturally occurring occurring vitamin D analogue with antiproliferative properties. Astrogorgiadiol was isolated from a Japanese marine sponge of the genus Astrogorgia (Fusetani et al. (1989) Tetrahedron Letters 30(50): 7079-7082), and was found to inhibit cell division of starfish eggs. Synthesis of astrogordiadiol was reported in Taber, D. F. and Malcolm, S. C. (2001) Journal of Organic Chemistry 66: 944-954, the disclosures of which are hereby incorporated by reference.

SUMMARY OF THE INVENTION

The present invention provides methods of downregulating osteopontin comprising administering to a cell or mammal an amount of astrogorgiadiol effective to downregulate production of mRNA encoding osteopontin.

The invention also provides methods of reducing production of osteopontin comprising administering to a cell or mammal an amount of astrogorgiadiol effective to reduce production of osteopontin.

Another aspect of the invention provides methods of treating osteoporosis comprising administering to a patient in need of such treatment a therapeutically effective amount of astrogorgiadiol. Optionally, an additional compound useful for treatment of osteoporosis can be administered in conjunction with astrogorgiadiol to the patient.

A further aspect of the invention provides methods of treating an autoimmune disease comprising administering to a patient in need of such treatment a therapeutically effective amount of astrogorgiadiol. Preferably, the autoimmune disease is systemic lupus erythematosis or multiple sclerosis. Optionally, an additional compound useful for treatment of an autoimmune disease can be administered in conjunction with astrogorgiadiol to the patient, Yet another aspect of the invention provides a pharmaceutical composition comprising astrogorgiadiol and a pharmaceutically acceptable carrier or diluent.

DETAILED DESCRIPTION OF THE INVENTION

Figure 1:
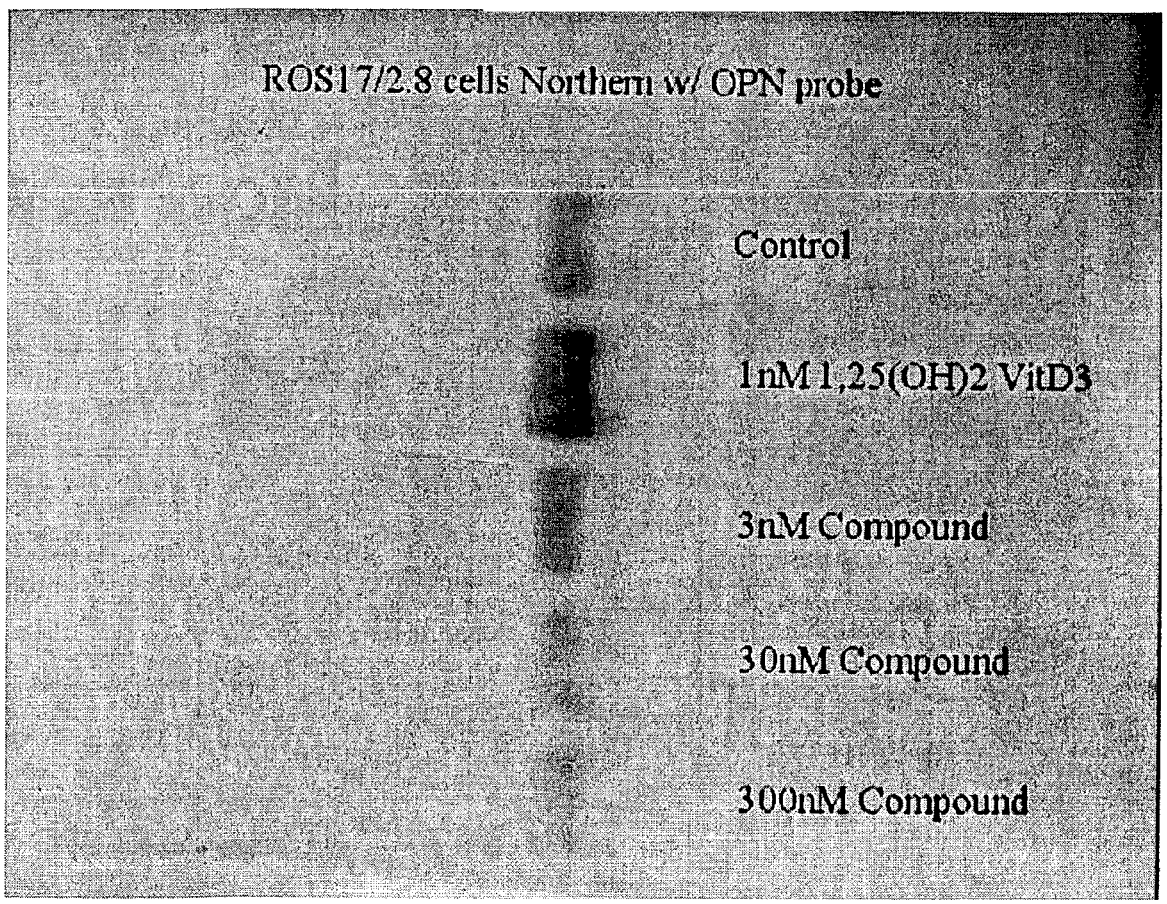
FIG. 1 shows a Northern blot of mRNA from ROS 17/2.8 cells cultured with 1 nM 1,25 (OH)2 VitD3 or 1 nM 1,25 (OH)2 VitD3 and 3 nM, 30 nM or 300 nM compound, i.e. astrogorgiadiol.

The present invention provides methods of downregulating osteopontin comprising administering to a cell or mammal an effective amount of astrogorgiadiol to downregulate mRNA production. Applicants have discovered that astrogorgiadiol downregulates production of osteopontin RNA and would therefore be useful for treating diseases associated with increased production of osteopontin such as osteoarthritis, and autoimmune disease, including systematic lupus erythamatosus and multiple sclerosis.

The present invention also provides a method of reducing production of osteopontin comprising administering to a cell or mammal an amount of astrogorgiadiol effective to reduce production of osteopontin.

The invention further provides methods of treating osteoporosis and autoimmune disease comprising administering to a patient in need of such treatment a therapeutically effective amount of astrogorgiadiol. Preferably, the autoimmune disease is systemic lupus erythematosis or multiple sclerosis.

The term effective amount and similar terms used herein refer to amounts of astrogorgiadiol that downregulate (i.e., decrease) levels of osteopontin RNA in cells. In the diseases with which osteopontin has been associated, the osteopontin RNA transcripts are increased in comparison with osteopontin levels in the absence of the disease. Downregulation of osteopontin RNA by astrogorgiadiol decreases the number of RNA transcripts or the frequency of translation, or both, below levels found in the disease state, or to levels found in the absence of the disease state.

The term therapeutically effective amount refers to an amount of a compound or combination of compounds that ameliorates, attenuates or eliminates one or more symptoms of a particular disease or condition or prevents or delays the onset of one or more symptoms or a particular disease or condition.

The term patient means animals, such a dogs, cats, cows, horses, sheep and humans. Preferred patients are mammals, more preferably humans.

The methods of the invention are useful for treatment of mammals, including humans. The terms "treating", "treat", "treatment", as used herein, include curative, preventative (e.g., prophylactic) and palliative treatment.

Astrogorgiadiol is a vitamin D derivative and has the structure shown below.

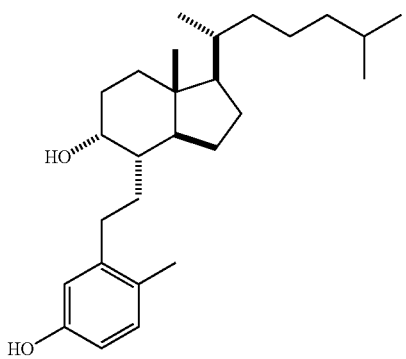

Astrogorgiadiol can be prepared according to the method of D. F. Taber and S. C. Malcolm, Journal of Organic Chemistry 66: 944-953, 2001, the disclosures of which are hereby incorporated by reference in their entirety.

Astrogorgiadiol can be used to downregulate osteopontin RNA in vitro in cells or in vivo in mammals. Preferably, for in vivo applications, the cells are mammalian cells that secrete osteopontin, including activated T cells, macrophages, osteoblasts and hypertrophic chondrocytes. Astrogorgiadiol is administered to the cells by any route that allows uptake of the compound by the cells. Typically, the astrogorgiadiol is in an aqueous solution that is added to the tissue culture or other medium containing the cells. It has been found that 3-300 nM astrogorgiadiol is effective to downregulate osteopontin RNA production, but other amounts of astrogorgiadiol can also be used.

Astrogorgiadiol is administered to a patient in a therapeutically effective amount. Astrogorgiadiol can be administered to the patient alone or as part of a pharmaceutical composition or formulation. Astrogorgiadiol can be administered all at once, as for example, by a bolus injection, or multiple times, such as by a series of tablets.

Astrogorgiadiol is generally administered to a patient in the form of a pharmaceutical composition comprising astrogorgiadiol and a pharmaceutically acceptable carrier or diluent.

For oral administration a pharmaceutical composition can take the form of solutions, suspensions, tablets, pills, capsules and powders. Tablets containing various excipients such as sodium citrate, calcium carbonate and calcium phosphate are employed along with various disintegrants such as starch and preferably potato or tapioca starch and certain complex silicates, together with binding agents such as polyvinylpyrrolidone, sucrose, gelatin and acacia. Additionally, lubricating agents such as magnesium stearate, sodium lauryl sulfate and talc are often very useful for tabletting purposes. Solid compositions of a similar type are also employed as fillers in soft and hard-filled gelatin capsules; preferred materials in this connection also include lactose or milk sugar as well as high molecular weight polyethylene glycols.

When aqueous suspensions and/or elixirs are desired for oral administration, astrogorgiadiol can be combined with various sweetening agents, flavoring agents, coloring agents, emulsifying agents and/or suspending agents, as well as such diluents as water, ethanol, propylene glycol, glycerin and various like combinations thereof. For purposes of parenteral administration, solutions in sesame or peanut oil or in aqueous propylene glycol can be employed, as well as sterile aqueous solutions of the corresponding water-soluble salts. Such aqueous solutions may be suitably buffered, if necessary, and the liquid diluent first rendered isotonic with sufficient saline or glucose. These aqueous solutions are especially suitable for intravenous, intramuscular, subcutaneous and intraperitoneal injection purposes. In this connection, the sterile aqueous media employed are all readily obtainable by standard techniques well-known to those skilled in the art. For purposes of transdermal (e.g., topical) administration, dilute sterile, aqueous or partially aqueous solutions (usually in about 0.1% to 5% concentration), otherwise similar to the above parenteral solutions, are prepared.

Methods of preparing various pharmaceutical compositions with a certain amount of active ingredient are known, or will be apparent in light of this disclosure, to those skilled in this art. For examples, see Remington's Pharmaceutical Sciences, Mack Publishing Company, Easter, Pa., 15th Edition (1995).

Pharmaceutical compositions according to the invention may contain from about 0.01 to about 90 percent of astrogorgiadiol, more preferably from about 5 to about 20 percent of astrogorgiadiol. In any event, the composition or formulation to be administered will contain sufficient astrogorgiadiol such that, after one or more doses of the pharmaceutical composition, a therapeutically effective amount of astrogorgiadiol is present in the patient.

Astrogorgiadiol can be administered to a patient at dosage levels in the range of about 0.1 mg to about 400 mg per day. For a normal adult human having a body weight of about 70 kg, a daily dosage in the range of about 0.01 to about 20 mg per kilogram body weight is typically sufficient. The specific dosage and dosage range of astrogorgiadiol that can be used depends on a number of factors, including the requirements of the patient, the severity of the condition or disease being treated, and the manner of administration. The determination of dosage ranges and optimal dosages for a particular patient is well within the ordinary skill in the art in light of this disclosure.

Administration of astrogorgiadiol can be via any method which delivers the compound systemically and/or locally. These methods include oral routes, parenteral, intraduodenal routes, etc.

In addition, astrogorgiadiol can be administered in conjunction with other pharmaceutically active compounds useful for treating osteoporosis or autoimmune disease. If the patient is to receive or is receiving multiple pharmaceutically active compounds, the compounds can be administered simultaneously, or sequentially. For example, in the case of tablets, the active compounds may be found in one tablet or in separate tablets, which can be administered at once or sequentially in any order. In addition, it should be recognized that the compositions may be different forms. For example, one or more compounds may be delivered via a tablet, while another is administered via injection or orally as a syrup. All combinations, delivery methods and administration sequences are contemplated. If astrogorgiadiol is administered in conjunction with other therapeutic agents, the proportions of astrogorgiadiol and other therapeutic agent being administered will be dependent on the particular disease state being addressed.

Representative agents that can be used in conjunction with astrogorgiadiol for treatment of osteoporosis include bisphosphonates, estrogens, calcitonin and raloxifene.

Representative agents that can be used in conjunction with astrogorgiadiol for treatment of multiple sclerosis include interferon 1beta and steroids.

Representative agents that can be used in conjunction with astrogorgiadiol for treatment of systemic lupus erythematosus include corticosteroids, non-steroidal anti-inflammatory agents (NSAIDs), antimalarial drugs such a hydroxychloroquine, immunosuppressants such as methotrexate and cyclophosphamide and hormone treatments.

EXAMPLES

Example 1

Synthesis of Astrogorgiadiol

Astrogorgiadiol can be prepared according to the method disclosed in D. F. Taber and S. C. Malcolm, Journal of Organic Chemistry 66:944-953, 2001, the disclosures of which are hereby incorporated by reference, as follows. Compound numbers refer to the corresponding compound in the synthetic schemes.

$^1$H NMR and $^{13}$C NMR spectra were obtained as solutions in deuteriochloroform (CDCl$_3$). $^{13}$C multiplicities were determined with the aid of a JVERT pulse sequence, differentiating the signals for methyl and methine carbons as "d" from methylene and quaternary carbons as "u". The infrared (IR) spectra were determined as neat oils. Mass spectra (MS) were obtained at an ionizing potential of 15 eV. Substances for which C,H analyses are not reported were purified as specified and gave spectroscopic data consistent with being >95% the assigned structure. Optical rotations were determined as solutions in dichloromethane unless otherwise noted. R$_f$ values indicated refer to thin layer chromatography (TLC) on 2.5×10 cm, 250 μm analytical plates coated with silica gel GF, unless otherwise noted, and developed in the solvent system indicated. All glassware was flame dried under a dry nitrogen stream before use. Tetrahydrofuran (THF), diethyl ether and 1,2-dimethoxyethane (DME) were distilled from sodium/benzophenone ketyl under dry nitrogen. Dichloromethane (CH$_2$Cl$_2$) and toluene were distilled from calcium hydride under dry nitrogen. All reaction mixtures were stirred magnetically, unless otherwise noted.

(R)-Citronellol (6): Powdered LiAlH$_4$ (12.5 g, 329 mmol) was introduced into a 5 L round bottom flask along with 2 L of THF (dried over 3 Å molecular sieve). The slurry was stirred mechanically under N$_2$ and the temperature was lowered to 0° C. (R)-citronellal (5, Takasago, Rockleigh, N.J.) (100 g, 648 mmol) was added neat over about 15 min and the residue was rinsed into the flask with an additional 500 mL of THF. Notwithstanding the fact that TLC indicated complete consumption of citronellal, the mixture was warmed to a gentle reflux and subsequently cooled to 0° C. The reaction was worked up by sequential dropwise addition of the following to the vigorously stirring mixture: 12.5 mL water, 12.5 mL 3 M NaOH, and a solution of 37.5 mL water in 37.5 mL THF. After filtration through celite and thorough washing of the solids with MTBE, the solvent was evaporated to yield 116 g of crude citronellol. This oil was distilled (bulb-to-bulb, 120-140° C., 0.8 mm Hg) to give 6 (93.4 g, 92%) as a clear oil, TLC R$_f$ (10% MTBE/petroleum ether) =0.09. $^1$H NMR (CDCl$_3$) (δ): 5.10 (m, 1H), 3.66 (m, 2H), 2.1-1.8 (m, 3H), 1.68 (s, 3H), 1.7-1.5 (m, 2H), 1.60 (s, 3H), 1.4-1.3 (m, 2H), 1.17 (m, 1H), 0.90 (d, J=6.66 Hz, 3H); $^{13}$C NMR (CDCl$_3$) (δ): u: 131.2, 61.0, 39.8, 37.1, 25.4; d: 124.6, 29.1, 25.6, 19.4, 17.6; IR (cm$^{-1}$): 3331 (b), 2927, 1454, 1377, 1058; MS (m/z, %): 55 (64), 69 (100), 82 (44), 95 (33), 109 (14), 123 (18), 138 (6), 156 (6); HRMS calcd for C$_{10}$H$_{20}$O: 156.1514. Found: 156.1514; [α]$_D^{17}$=+3.74 (c 1.02, EtOH).

(S)-Methyl 2-Diazo-7,11-dimethyl-3-oxo-10-dodecenoate (1): A solution of citronellol 6 (30.0 g, 192 mmol) in 400 mL CH$_2$Cl$_2$ was allowed to stir at 0° C. under N$_2$ in a 1 L round bottom flask. Triethylamine (60 mL, 430 mmol) was added in one portion, followed by DMAP (2.0 g, 1.64 mmol). Finally, benzenesulfonyl chloride (30 mL, 240 mmol) was added dropwise via syringe. After the mixture was stirred for 2 h at 0° C., it was partitioned between petroleum ether and, sequentially, 3 M aqueous HCl, water, and brine. The organic layer was dried (Na$_2$SO$_4$) and the solvent was removed in vacuo at 30° C. Removal of residual solvent under high vacuum yielded citronellyl benzenesulfonate (62.4 g, 110% of theoretical) as a clear yellow oil, TLC R$_f$(10% MTBE/petroleum ether)=0.41. $^1$H NMR (CDCl$_3$) (δ): 7.92 (m, 2H), 7.66 (m, 1H), 7.56 (m, 2H), 5.03 (m, 1H), 4.09 (m, 2H), 1.91 (m, 2H), 1.68 (m, 1H), 1.67 (s, 3H), 1.57 (s, 3H), 1.52 (m, 1H), 1.44 (m, 1H), 1.24 (m, 1H), 1.11 (m, 1H), 0.81 (d, J=6.49 Hz, 3H); $^{13}$C NMR (CDCl$_3$) (δ): u: 136.1, 131.4, 69.2, 36.6, 35.5, 25.1; d: 133.6, 129.1, 127.7, 124.2, 28.7, 25.6, 18.9, 17.5; IR (cm$^{-1}$): 2914, 1449, 1360, 1188, 944.

Sodium hydride (30 g, 60% in mineral oil, 750 mmol) was suspended in 400 mL of THF in a 1 L-3 neck round bottom flask fitted with a mechanical stirrer. The slurry was cooled in an ice-water bath and methyl acetoacetate (46 mL, 426 mmol) was added rapidly dropwise. After the addition was complete, the mixture was stirred for 10 min, then n-BuLi (165 mL, 2.33 M in hexanes, 384 mmol) was added rapidly dropwise. The mixture spontaneously warmed to reflux and then cooled over the next 10 min. Finally, a solution of the crude citronellyl benzenesulfonate (192 mmol theoretical) in 100 mL of THF was added via cannula, and the mixture was stirred at room temperature for 1 hour. The mixture was quenched cautiously by pouring into saturated aqueous NH$_4$Cl before being partitioned between MTBE and, sequentially, water and brine. The solvent was removed in vacuo, yielding 67 g of a yellow oil. The residue was distilled (bulb-to-bulb, 140-160° C., 0.8 mm Hg) to yield crude 8 (31.3 g, 64% of theoretical based on citronellol) as a yellow oil, TLC R$_f$(10% MTBE/petroleum ether)=0.37. $^1$H NMR (CDCl$_3$) (δ): 5.08 (m, 1H), 3.74 (s, 3H), 3.45 (s, 2H), 2.52 (t, J=7.34 Hz, 2H), 1.96 (m, 2H), 1.68 (s, 3H), 1.60 (s, 3H), 1.6-1.2 (m, 6H), 1.13 (m, 1H), 0.87 (d, J=6.85 Hz, 3H); $^{13}$C NMR (CDCl$_3$) (δ): u: 202.6, 167.5, 130.9, 48.0, 43.2, 36.8, 36.1, 25.3, 20.0; d: 124.7, 52.1, 32.1, 25.6, 19.2, 17.5; IR (cm$^{-1}$): 2925, 1748, 1716.

Triethylamine (42 mL, 301 mmol) and mesyl azide (18 g, 149 mmol) were added to a solution of the acetoacetate 8 in CH$_3$CN (130 mL). Although the reaction is usually complete in two hours under these conditions, in this case, the mixture was allowed to stir overnight. One half of the solvent was removed using a rotovap (50° C.) and the remaining liquid was partitioned between petroleum ether and, sequentially, 3 M aqueous NaOH and brine. The solvent was removed in vacuo, leaving 36.8 g of a brown oil. The residue was chromatographed and the purest fraction provided 1 (26.4 g, 49% from citronellol) as a pale yellow oil, TLC R$_f$(10% MTBE/petroleum ether)=0.47. $^1$H NMR (CDCl$_3$) (δ): 5.09 (m, 1H), 3.84 (s, 3H), 2.83 (t, J=7.85 Hz, 2H), 1.96 (m, 2H), 1.68 (s, 3H), 1.60 (s, 3H), 1.7-1.5 (m, 2H). 1.5-1.3 (m, 3H), 1.15 (m, 2H), 0.88 (d, J=6.49 Hz, 3H); $^{13}$C NMR (CDCl$_3$) (δ): u: 193.0, 161.8, 131.1, 40.5, 36.9, 36.4, 25.5, 21.9; d: 124.9, 52.1, 32.2, 25.7, 19.4, 17.6; IR (cm$^{-1}$): 2914, 2133, 1725, 1659, 1309. This substance was not stable to analysis by mass spectrometry.

Methyl 5-Dimethylhexenyl-2-oxocyclopentanecarboxylate (2) via Rh$_2$Oct$_4$ Catalysis: The CH$_2$Cl$_2$ used in the following reaction was distilled from CaH$_2$ and passed through a column (20×150 mm) of anhydrous K$_2$CO$_3$ prior to use. The α-diazo-β-ketoester 1 (25.5 g, 101 mmol) was dissolved in 1 L CH$_2$Cl$_2$. A solution of rhodium octanoate (400 mg, 0.56 mol %) in 5 mL dry CH$_2$Cl$_2$ was added in one portion. The solution was allowed to stir for 12 hours before being evaporated. The green residue was chromatographed to provide cyclopentanone 2 (17.0 g, 74%) as a light-green oil. Bulb-to-bulb distillation (170° C. at 0.4 mm Hg) yielded a clear oil which formed moist crystals on standing. These did not show a sharp melting point. TLC R$_f$(10% MTBE/petroleum ether)=0.28. $^1$H NMR (CDCl$_3$) (δ): 5.06 (m, 1H), 3.75 (s, 3H), 2.97 (d, J=11.6 Hz, 0.43H), 2.95 (d, J=11.3 Hz, 0.57H), 2.55 (m, 1H), 2.5-2.3 (m, 2H), 2.3-1.9 (m, 3H), 1.69 (s, 3H), 1.61 (s, 3H), 1.6-1.3 (m, 3H), 1.17 (m, 1h), 0.93 (d, J=6.83 Hz, 1.3H), 0.91 (d, J=6.85 Hz, 1.7H); $^{13}$C NMR (CDCl$_3$) (δ): (Major) u: 212.4, 170.7, 131.7, 38.7, 33.8, 25.3, 25.1; d: 124.2, 59.6, 52.4, 46.7, 36.8, 25.7, 17.6, 16.9; $^{13}$C NMR (CDCl$_3$) (δ): (Minor) u: 212.2, 170.3, 131.6, 38.5, 33.8, 25.3, 25.1; d: 124.1, 59.7, 52.4, 46.3, 35.7, 25.7, 15.5, 16.9; IR (cm$^{-1}$): 3447 (br), 2966, 1757, 1726.

Integration of the peaks (59.6 versus 59.7) and (46.7 versus 46.3) indicated a 1.4:1.0 mixture of components (14% de). The result was nicely corroborated by GC-FID. Samples were analyzed on a Hewlett-Packard HP6890 Gas Chromatograph using a Chiraldex γ-cyclodextrin trifluoroacetyl capillary GC column (30 m×0.25 mm). Signals were obtained from a flame-ionization detector. Upon injection of the sample (5 μL of a 1 mg/mL solution in ethyl acetate), the oven temperature was maintained at 50° C. for 20 min. Then the temperature was increased at 1° C./min for 100 min. For the methyl ester, the peaks at t=95.5 (minor) and t=96.6 (major) integrated at 43:57 (14% de). The dimethylpentyl ester was detected at t=97.3 (minor) and t=98.9 (major).

Recrystallization was effected by adding 1 g of the crude 2 to 10 mL of ethanol and 10 mL water and heating to 50° C. More ethanol was added to the oily mixture as it was maintained at this temperature until all the oil was dissolved (up to an additional 10 mL). Seeding can be helpful but, usually, cooling to room temperature produced significantly diastereomerically-enriched material (>99% de) as white flakes, mp=58-59° C. $^1$H NMR (CDCl$_3$) (δ): 5.07 (m, 1H), 3.75 (s, 3H), 2.95 (d, J=11.26 Hz, 1H), 2.55 (m, 1H), 2.5-2.3 (m, 2H), 2.20 (m, 1H), 2.06 (m, 1H), 1.94 (m, 1H), 1.69 (s, 3H), 1.61 (s, 3H), 1.6-1.4 (m, 3H), 1.16 (m, 1h), 0.91 (d, J=6.85 Hz, 3H); $^{13}$C NMR (CDCl$_3$) (δ): u: 212.4, 170.7, 131.7, 38.7, 33.8, 25.3, 25.1; d: 124.2, 59.6, 52.4, 46.7, 36.8, 25.7, 17.6, 16.9; IR (cm$^{-1}$): 2969, 1744, 1724, 1287, 1118; MS (m/z, %): 55(26), 69 (36), 81(10), 109 (60), 141(100), 168 (5), 220 (13), 252 (2); HRMS calcd for C$_{15}$H$_{24}$O$_3$: 252.1725; found: 252.1731; [α]$_D^{17}$ =−51.45 (c 1.14, EtOH).

Rh$_2$(S)-PTPA$_4$: (R)-(+)-Phenylalanine (500 mg, 3.03 mmol) and phthalic anhydride (500 mg, 3.38 mmol) were combined in a test tube. Three times the solid was heated until it melted and then was allowed to cool. The solid was recrystallized from 50% ethanol/water (5 mL) to yield (R)-N-phthaloylphenylalanine (0.65 g, 73%) as a white solid. Mp=179-180° C. The (R)-N-phthaloylphenylalanine (600 mg, 2.03 mmol) and rhodium trifluoroacetate (164 mg, 0.25 mmol) were combined in a round-bottomed flask. Three times the solid was dissolved in dichloroethane (20 mL) and heated to dryness under a stream of nitrogen. The green oil was chromatographed. The major green fraction was collected and recrystallized from 10% acetone/heptane (5 mL) to give small green needles (114 mg, 33% based on rhodium added). TLC R$_f$(1:1:3 acetone: CH$_2$Cl$_2$: petroleum ether)=0.28.

The mother liquor was combined with the other column fractions and evaporated. More rhodium trifluoroacetate was added (100 mg, 0.15 mmol). Two times the sample was dissolved in dichloroethane (20 mL) and heated to dryness under a stream of nitrogen. The green oil was dissolved in hot 2:1 methanol/CH$_2$Cl$_2$ (30 mL). Overnight a large mass of green crystals separated. These were collected and dissolved in CH$_2$Cl$_2$ (10 mL). Methanol was added (30 mL) and the solution was allowed to sit overnight in an open container. Large green crystals separated and were collected. The crystals (presumably the methanol adduct of the catalyst) were dissolved in ethyl acetate to displace the methanol. Then, all of the solvent was removed by heating in vacuo to yield Rh$_2$(S) PTPA$_4$ (150 mg, 27% additional yield based on total rhodium added) as a mint green powder.

Methyl 5-dimethylhexenyl-2-oxocyclopentanecarboxylate (2) via Rh$_2$(S)-PTPA$_4$ Catalysis: The α-diazo-β-ketoester 1 (2.00 g, 7.13 mmol) was dissolved in 100 mL of CH$_2$Cl$_2$ (dry—see above) and a solution of Rh$_2$(S)-PTPA$_4$ (47.8 mg, 0.48 mol %) in 5 mL of CH$_2$Cl$_2$ was added rapidly dropwise. After two hours at room temperature, the solvent was evaporated and the green residue was chromatographed to yield 2 (1.73 g, 96%) as a clear oil. The mixture thus obtained was a 74:26 mixture of (R, R)-2 and (S, R)-2 (48% de). The product was distilled and crystallized as above to yield (R, R)-2 (722 mg, 40%) that was diastereomerically-pure by $^1$H and $^{13}$C NMR.

(S)-RuBINAP hydrogenation: A 5 mL reactivial was charged with [RuCl$_2$(COD)]$_n$ (39 mg, 0.139 mmol), (S)-BINAP (100 mg, 0.151 mmol), triethylamine (200 mg, 1.98 mmol), and toluene (4 mL). The vial was sealed and heated in a 140° C. oil bath for 3 h. The solution was allowed to cool slightly and transferred to a round bottom flask (rinsing with hot THF) under a N$_2$ stream. The volatile material was removed in vacuo to yield a brown solid. This material was dissolved in THF (10 mL) to provide a 13.9 mM (S)-RuBINAP solution.

Cyclopentanone 2 (5.07 g, 20.1 mmol, 14% de) was dissolved in MeOH (100 mL) in a modified Parr bottle. Water (0.5 mL, 28 mmol) and a solution of HCl in MeOH (5.0 mL of a stock solution made from 1 mL concentrated aqueous HCl and 99 mL of MeOH, 0.60 mmol) were added and the solution was purged with N$_2$ for 5 min. The 13.9 mM (S)-RuBINAP solution (10 mL, 0.69 mol % based on 2) prepared above was added. Four times the flask was evacuated using a water aspirator and then refilled with H$_2$ (10 psig) causing the green solution to turn brown. The flask was heated in a 60° C. oil bath with vigorous stirring under an H$_2$ atmosphere until the starting material was about half consumed (2 h, TLC). The mixture was transferred to a round bottom flask and the solvent was removed in vacuo. The residue was diluted in $CH_2Cl_2$ (100 mL). Flash silica gel (10 g) and 3 M aqueous HCl (1 mL) were added and the mixture was allowed to stir for 30 min. The solvent was then evaporated and the resultant solid was chromatographed to yield the recovered cyclopentanone 2 (2.10 g, 84% de, 66% recovery of this diastereomer) as a clear oil. Also isolated was the reduced compound 11 (2.64 g, 90% yield based on 2 not recovered) as a green oil, TLC $R_f$ (50% MTBE/petroleum ether)=0.51.

An analogous experiment that was not vigorously stirred yielded moderately enriched 2 (3.06 g, 78% de, 47% recovery of this diasteromer). Recrystallization was effected by adding this recovered 2 to 24 mL of ethanol and 12 mL water and heating to 30° C. The temperature was reduced to 20° C. and the solution was seeded with a few 97% de crystals. The solution was cooled to -5° C. over 15 min which produced large crystals. The solution was further cooled to -20° C. and filtered. The crystals were rinsed with a few mL of cold 50% aqueous EtOH and dried in vacuo to give significantly diastereomerically-enriched 2 (1.46 g, 99% de, 29% overall recovery of this diastereomer) as white flakes, mp=58-59° C. $^1$H NMR ($CDCl_3$) δ 5.07 (m, 1H), 3.75 (s, 3H), 2.95 (d, J=11.26 Hz, 1H), 2.55 (m, 1H), 2.5-2.3 (m, 2H), 2.20 (m, 1H), 2.06 (m, 1H), 1.94 (m, 1H), 1.69 (s, 3H), 1.61 (s, 3H), 1.6-1.4 (m, 3H), 1.16 (m, 1h), 0.91 (d, J=6.85 Hz, 3H); $^{13}$C NMR ($CDCl_3$) δ u: 212.4, 170.7, 131.7, 38.7, 33.8, 25.3, 25.1; d: 124.2, 59.6, 52.4, 46.7, 36.8, 25.7, 17.6, 16.9; IR ($cm^{-1}$): 2969, 1744, 1724, 1287, 1118; MS (m/z, %): 55(26), 69 (36), 81 (10), 109 (60), 141 (100), 168 (5), 220 (13), 252 (2); HRMS calcd for $C_{15}H_{24}O_3$: 252.1725; found: 252.1731; $[α]_D^{17}$=-51.45 (c 1.14, EtOH).

4-Methyl-3-(4-hydroxybutyl)anisole (16): A three neck round bottom flask was charged with magnesium (4.2 g, 102.0 mmol), a few crystals of iodine and 15 mL of THF. The mixture was heated until the iodine color was discharged, then cooled to 0° C. A solution of allyl chloride (2.8 mL, 34.35 mmol) in 20 mL of THF was added slowly dropwise over about an hour and a half. After the addition was complete, the grey solution was warmed to reflux briefly and then cooled back down to 0° C. This Grignard solution was added rapidly dropwise via cannula to a solution of dibromide 15 (4.75 g, 16.96 mmol) in 35 mL of THF which was stirring at 0° C. After 30 min, the solution was quenched cautiously with saturated aqueous $NH_4Cl$ and partitioned between MTBE and, sequentially, water and brine. The combined organic extract was dried ($Na_2SO_4$) and evaporated to give crude 16 (3.96 g, 97% of expected) as a pale-yellow oil, TLC $R_f$(10% MTBE/petroleum Ether) =0.69. The NMR spectrum of 16 indicated that it was 95% pure. $^1$H NMR ($CDCl_3$) (δ): 7.33 (d, J=8.53 Hz, 1H), 6.69 (d, J=3.07 Hz, 1H), 6.55 (dd; J=8.53, 3.07 Hz, 1H), 5.80 (m, 2H), 5.00 (d, J=17.1 Hz, 1H), 4.93 (d, J=10.2 Hz, 2H), 3.70 (s, 3H), 2.70 (m, 2H), 2.29 (m, 2H); $^{13}$C NMR ($CDCl_3$) (δ): u: 158.8, 142.0, 115.2, 114.9, 35.8, 33.8; d: 137.6, 133.2, 116.1, 112.4, 55.4; IR($cm^{-1}$): 2934, 1571, 1472, 1241, 1017; MS(m/z, %): 63 (21), 77 (44), 91 (38), 105 (15), 120 (32), 147 (10), 161 (100), 171 (16), 199 (84), 201 (82), 240 (41), 242 (40); HRMS calcd for $C_{11}H_{13}BrO$: 240.0149; found: 240.0136. ~5% of the biaryl could be separated as a white solid, TLC $R_f$(10% MTBE/petroleum ether)=0.53. $^1$H NMR ($CDCl_3$) (δ): 7.44 (d, J=8.53 Hz, 2H), 6.72 (d, J=3.07 Hz, 2H), 6.65 (dd, J=8.53, 3.07 Hz, 2H), 3.78 (s, 6H), 3.96 (s, 4H).

A round bottom flask was charged with a 2M solution of $BH_3DMS$ in THF (15 ml, 30 mmol) and cooled to 0° C. A solution of cyclohexene (6.0 mL, 59.22 mmol) in 15 mL of THF was added dropwise. The cooling bath was removed and the mixture was allowed to stir at ambient temperature for one hour. A solution of crude alkene 16 (15.42 mmol theoretical) in 15 mL of THF was added in one portion and the resultant mixture was allowed to stir for two hours. At this time, the mixture was quenched by cautious addition of ethanol (17 mL), 3 M aqueous NaOH (17 mL), and 30% $H_2O_2$ (51 mL) and allowed to stir overnight. The mixture was partitioned between saturated aqueous $NH_4Cl$ and MTBE, dried over $Na_2SO_4$, and evaporated. Bulb-to-bulb distillation (60° C. at 0.5 mm Hg) of the residue afforded 17 (5.6 g. 140% of expected) as a yellow oil. The material is contaminated with residual cyclohexanol but was used directly in the next step. An analytically-pure sample was obtained by chromatography: TLC $R_f$ (50% MTBE/petroleum ether)=0.27. $^1$H NMR ($CDCl_3$) (δ): 7.38 (d, J=8.53 Hz, 1H), 6.76, (d, J=3.07 Hz, 1H), 6.61 (dd, J=8.53, 3.07 Hz, 1H), 3.76 (s, 3H), 3.70 (m 21H), 2.72 (m, 2H), 1.68 (m, 3H); $^{13}$C NMR ($CDCl_3$) (δ): u: 158.7, 142.4, 114.7, 62.4, 35.9, 32.1, 25.9; d: 133.1, 115.9, 112.9, 55.3; IR($cm^{-1}$): 3347(b), 1595, 1572, 1472, 1241; MS (m/z, %): 77(24), 91 (25), 105 (11), 121 (47), 146 (9), 161 (100), 178 (8), 199 (28), 201 (26), 212 (35), 214 (30), 258 (36), 260 (31); HRMS calcd for $C_{11}H_{15}BrO_2$: 258.0255. Found: 258.0255.

The crude 17 (15.42 mmol theoretical) was diluted with 140 mL of dry ether and cooled to 0° C. $NiCl_2$(dppp) (180 mg, 0.314 mmol) was added to produce a red suspension. A 3 M solution of MeMgBr in ether (11.3 mL, 33.9 mmol) was added dropwise to produce, initially, a milky white precipitate. After about ⅔ of the Grignard had been added, the red particles became sticky and adhered to the walls of the flask. As the solution was warmed to reflux, the red particles were dissolved and the liquid turned yellow. The reaction was monitored over the next 84 hours as additional amounts of catalyst and Grignard were added to complete the reaction. The mixture was cooled and quenched with saturated aqueous $NH_4Cl$ solution, extracted with ether, and washed with brine. The organic layer was dried over $Na_2SO_4$ and the solvent removed in vacuo. Bulb-to-bulb distillation (170-180° C. at 0.5 mm Hg) afforded 18 (2.27 g, 76% yield from dibromide) as a clear oil, TLC $R_f$(50% MTBE/petroleum ether)=0.34. $^1$H NMR ($CDCl_3$) (δ): 7.03 (d, J=8.19 Hz, 1H), 6.71 (d, J=2.73 Hz, 1H), 6.65 (dd, J=8.19, 2.73 Hz, 1H), 3.77 (s, 3H), 3.67 (d, J=6.94 Hz, 2H), 2.59 (m, 2H), 2.22 (s, 3H), 1.64 (m, 2H); $^{13}$C NMR ($CDCl_3$) (δ): u: 157.7, 141.2, 127.9, 62.2, 33.8, 29.6; d: 130.8, 114.6, 110.7, 55.1, 18.2; IR($cm^{-1}$): 3361 (br), 2936, 1609, 1499, 1252, 1036; MS (m/z, %): 65 (11), 77 (16), 79 (11), 91 (28), 105 (10), 121 (35), 123 (27), 135 (100), 136 (43), 148 (20), 149 (11), 161 (9), 176 (8), 194 (53); HRMS calcd for $C_{12}H_{18}O_2$: 194.1307. Found: 194.1301.

The material was contaminated with about 5% of the corresponding desmethyl compound which could not be efficiently separated by column chromatography: $^1$H NMR (δ): 7.18 (t, 7.85 Hz, 1H), 6.7-6.8 (m, 2 H), 3.77 (s, 3H); $C^{13}$C NMR (δ): (u): 159.4, 143.9; (d): 129.1, 120.7, 114.1, 110.8, 55.0.

Enone 20: The Dess-Martin periodinane (6.80 g, 16.03 mmol) was suspended in 40 mL of dry $CH_2Cl_2$ and a solution of arylbutanol 18 (3.10 g, 15.96 mmol) in 40 mL of $CH_2Cl_2$ was added to it. The white precipitate was dissolved immediately but reformed slowly. After 30 minutes at ambient temperature, the reaction was partitioned between ether and, sequentially, 1:1 10% aqueous $Na_2S_2O_3$/saturated aqueous NaHCO$_3$, water, and brine. The aqueous washes were back extracted with ether and washed with water and brine. The combined organic extracts were dried over Na$_2$SO$_4$, filtered through silica and evaporated to give crude 19 (3.64 g, 119% of expected) as a pale-yellow oil, TLC R$_f$ (50% MTBE/petroleum ether)=0.60. A sample was further purified by chromatography for analysis. $^1$H NMR (CDCl$_3$) (δ): 9.77 (t, J=1.71 Hz, 1H), 7.05 (d, J=8.19 Hz, 1H), 6.68 (m, 1H), 6.66 (d, J=2.73 Hz, 1H), 3.77 (s, 3H), 2.60 (m, 2H), 2.50 (dt, J=7.17, 1.71 Hz, 2H), 2.23 (s, 3H), 1.91 (m, 2H); $^{13}$C NMR (CDCl$_3$) (δ): u: 157.1, 140.6, 127.9, 43.3, 32.6, 22.3; d: 202.3, 131.0, 114.7, 111.0, 55.1, 18.3; IR (cm$^{-1}$): 2945, 1723, 1609, 1504, 1252; MS (m/z, %): 65 (17), 77 (23), 91 (41), 105 (13), 121 (42), 135 (100), 135 (50), 148 (45), 164 (26), 192 (39); HRMS calcd for C$_{12}$H$_{16}$O$_2$: 192.1150. Found: 192.1158.

The crude aldehyde 19 (15.95 mmol theoretical) was dissolved in 25 mL of THF and cooled to 0° C. A 1 M solution of commercial vinyl magnesium bromide (25 mL, 25.00 mmol) in THF was added dropwise. After 1 hour at 0° C., the mixture was partitioned between saturated aqueous NH$_4$Cl and MTBE, Dried over Na$_2$SO$_4$ and evaporated. Silica gel chromatography afforded the vinyl carbinol (2.02 g, 57% yield from alcohol 18) and alcohol 18 (0.48 g, 15% recovered). For the vinyl carbinol: TLC R$_f$(50% MTBE/petroleum ether)=0.56. $^1$H NMR (CDCl$_3$) (δ): 7.04 (d, J=8.19 Hz, 1H), 6.70 (d, J=2.73 Hz, 1H), 6.65 (dd, J=8.29, 2.73 Hz, 1H), 5.87 (ddd, J=17.07, 10.24, 6.49, 1H), 5.23 (dt, J=17.07, 1.37 Hz, 1H), 5.11 (dt, J=10.24, 1.37 Hz, 1H), 4.14 (m, 1H), 3.78 (s, 3H), 2.7-2.5 (m, 2H), 2.23 (s, 3H), 1.7-1.5 (m, 4H); $^{13}$C NMR (CDCl$_3$) (δ): (u): 157.7, 141.7, 127.9, 114.8, 36.8, 33.3, 25.9; (d): 141.1, 130.8, 114.7, 110.7, 73.2, 55.2, 18.4; IR (cm$^{-1}$): 3415 (br), 2934, 1609, 1499, 1251.

The crude vinyl carbinol was dissolved in 30 mL CH$_2$Cl$_2$ and Dess-Martin periodinane (3.90 g, 9.20 mmol) was added as a suspension in 20 mL CH$_2$Cl$_2$. The reaction warmed to reflux briefly on its own accord. After 30 minutes, the mixture was evaporated onto silica gel and chromatographed to afford enone 20 (1.72 g, 86% from the vinyl carbinol) as a clear oil. The three step yield (from alcohol 18) was 59% based on starting material not recovered. For 20: TLC R$_f$(50% MTBE/petroleum ether)=0.65; $^1$H NMR (CDCl$_3$) (δ): 7.04 (d, J=8.19 Hz, 1H), 6.69 (d, J=2.73 Hz, 1H), 6.65 (dd, J=8.19, 2.73 Hz, 1H), 6.35 (dd, J=17.4, 10.2 Hz, 1H), 6.19 (dd, J=17.8, 1.02 Hz, 1H), 5.80 (dd, J=10.2, 1.02 Hz, 1H), 3.76 (s, 3H), 2.64 (t, J=7.17 Hz, 2H), 2.59, (m, 2H), 2.23, (s, 3H), 1.90 (m, 2H); $^{13}$C NMR (CDCl$_3$)(δ): u: 200.4, 157.7, 140.9, 128.0, 127.8, 38.1, 32.6, 23.9; d: 136.4, 130.8, 114.6, 110.9, 55.1, 18.2; IR (cm$^{-1}$): 2945, 1681, 1612, 1500, 1253; MS (m/z, %): 91 (12), 135 (13), 136 (10), 148 (100), 218 (25); HRMS calcd for C$_{14}$H$_{18}$O$_2$: 218.1307. Found: 218.1303.

The three step yield for the same procedure using freshly prepared vinyl magnesium bromide (0.5M, 1.5 eq.) was 63%. There was no recovered alcohol 18.

The enone 20 prepared by the procedure outlined above was contaminated with about 5% of the desmethyl enone 22. These could be separated by formation of the crystalline phenoxy ketone 21.

Phenoxy ketone 21: NaH (25 mg, 1.1 mmol) was added in small portions to a solution of phenol (1 mL) in THF (1 mL). After 30 min, enone 20 (100 mg, 0.458 mmol) was added as a solution in 1 mL THF. The mixture was allowed to stir at ambient temperature for three hours before being partitioned between saturated aqueous NH$_4$Cl and MTBE. The organic layer was dried over Na$_2$SO$_4$ and the solvent was removed in vacuo. The residue was chromatographed and recrystallized (10% EtOAc/petroleum ether) to yield 21 (109 mg, 76%) as a white solid, mp=44.0-45.0° C. TLC R$_f$ (20% MTBE/petroleum ether)=0.41. $^1$H NMR (CDCl$_3$) (δ): 7.3 (m, 2H), 7.04 (d, J=8.19 Hz, 1H), 6.94 (t, J=7.17 Hz, 1H), 6.88 (d, J=8.53 Hz, 2H), 6.69 (d, J=2.73 Hz, 1H), 6.66 (dd, J=8.19, 2.73 Hz, 1H), 4.22 (t, J=6.14 Hz, 2H), 3.76 (s, 3H), 2.86 (t, J=6.14 Hz, 2H), 2.6 (m, 4H), 2.23 (s, 3H), 1.9 (m, 2H); $^{13}$C NMR (CDCl$_3$) (δ): u: 208.3, 158.5, 157.7, 140.9, 128.0, 62.8, 42.8, 42.1, 32.6, 23.6, 18.3; d: 130.9, 129.4, 120.9, 114.7, 114.4, 110.9, 55.2, 18.3; IR (cm$^{-1}$): 2939, 1714, 1600,1496, 1246. HRMS calcd for C$_{12}$H$_{24}$O$_3$: 312.1726. Found: 312.1720.

Methylated D-ring Chiron (23): To a solution of cyclopentanone 2 (2.00 g, 7.93 mmol) in 40 mL of acetone was added methyl iodide (1.0 mL, 16.06 mmol) and K$_2$CO$_3$ (4.0 g, 28.94 mmol). The mixture was heated to reflux for 5 hours before being cooled and partitioned between saturated aqueous NH$_4$Cl and EtOAc. The organic layer was dried over Na$_2$SO$_4$, filtered through silica, and evaporated. The residue was chrothatographed to yield the C-methylated compound 23 (1.80 g, 85%) as a clear oil, TLC R$_f$(10% MTBE/petroleum ether)=0.40. $^1$H NMR (CDCl$_3$) (δ): 5.08 (m, 1H), 3.67 (s, 3H), 2.57 (m, 1H), 2.24 (m, 1H), 2.15 (m, 1H), 2.04 (m, 1H), 2.0-1.7 (m, 3H), 1.69 (s, 3H), 1.61 (s, 3H), 1.49 (m, 2H), 1.40 (2, 3H), 1.15 (m, 1H), 1.01 (d, J=6.83 Hz); $^{13}$C NMR (CDCl$_3$) (δ): u: 216.9, 171.4, 131.4, 59.2, 37.5, 34.1, 25.1, 24.5; d: 124.3, 55.0, 51.8, 35.2, 25.6, 21.3, 18.2, 17.6; IR (cm$^{-1}$): 2967, 1753, 1732, 1222, 1172; MS (m/z, %): 67 (35), 82 (26), 97 (41), 109 (100), 123 (38), 137 (31), 160 (28), 188 (56), 219 (10), 233 (42), 248 (89), 266 (2); HRMS calcd for C$_{16}$H$_{26}$O$_3$: 266.188. Found: 266.1882.

Also isolated was the O-methylated compound (0.22 g, 10% yield) as a clear oil, TLC R$_f$(10% MTBE/petroleum ether)=0.07. $^1$H NMR (CDCl$_3$) (δ): 5.04 (m, 1H), 3.83 (s, 3H), 3.70 (s, 3H), 2.97 (m, 1H), 2.58 (m, 2H), 2.02 (m, 1H), 2.0-1.7 (m, 3H), 1.66 (s, 3H), 1.58 (s, 3H), 1.7-1.6 (m, 1H), 1.32 (m, 2H), 0.89 (d, J=6.83 Hz, 3H); $^{13}$C NMR (CDCl$_3$) (δ): u: 169.4, 165.6, 130.9, 106.3, 30.5, 30.3, 26.1, 20.6; d: 124.9, 57.5, 50.6, 47.7, 34.6, 25.6, 17.7, 17.5; IR (cm$^{-1}$): 2951, 1690, 1627, 1376, 1233, 1060; MS (m/z, %): 95 (12), 155 (100), 182 (10), 195 (13), 266 (16); HRMS calcd for C$_{16}$H$_{26}$O$_3$: 266.1882. Found: 266.1901.

The O-alkylated material (0.22 g, 0.827 mmol), as a solution in 30 mL THF, could be recycled by brief exposure to concentrated aqueous HCl (1 mL). After 15 minutes, the mixture was filtered through silica, evaporated, and chromatographed to give 2 (0.11 g, 53%) as clear oil. The overall yield of 23 then became 90% based on starting material not recovered.

Dimethylhexenyl-methylcyclopentanone (25): To a solution of methylated compound 23 (1.80 g, 6.76 mmol) in. 67 mL of HMPA was added NaCN (1.32 g, 26.93 mmol). The mixture was warmed to 75-80° C. for 5 hours before being partitioned between MTBE and, sequentially, saturated aqueous NaHCO$_3$ and water. The organic layer was evaporated. When chromatographed this stage, the mixture was found to contain about 10% of the diastereomeric cyanohydrins 24 in roughly equal amounts: TLC R$_f$(10% MTBE/petroleum ether)=0.16. $^1$H NMR (CDCl$_3$) (δ): 5.08 (m, 1H), 2.35 (br s, 1H), 2.2-1.7 (m, 6H), 1.69 (s, 3H), 1.60 (s, 3H), 1.6-1.5 (m, 2H), 1.3-1.2 (m, 2H), 1.10 (d, J=6.83 Hz, 3H), 0.93 (m, 1H), 0.80 (d, J=6.83 Hz, 3H); IR (cm$^{-1}$): 3438 (br), 2239 (w).

TLC R$_f$(10% MTBE/petroleum ether)=0.14. $^1$H NMR (CDCl$_3$) (δ): 5.08 (m, 1H), 2.66 (br s, 1H), 2.23 (m, 1H), 2.1-1.8 (m, 4H), 1.8-1.4 (m, 4H), 1.69 (s, 3H), 1.61 (s, 3H), 1.4-1.1 (m, 2H), 1.16 (d, J=6.83 Hz, 3H), 0.83 (d, J=6.83 Hz, 3H); IR (cm1): 3432 (br), 2239 (w).

The crude residue from decarbomethoxylation was instead diluted with 20 mL of 10% KOH in MeOH. After 5 minutes at ambient temperature, the mixture was partitioned between petroleum ether and, sequentially, water and brine. The organic layer was dried over $Na_2SO_4$ and evaporated. The residue was chromatographed to give ketone 25 (1.06 g, 75%) as a clear oil, TLC $R_f$(10% MTBE/petroleum ether) =0.46. 1H NMR ($CDCl_3$) (δ): 5.10 (m, 1H), 2.30 (dd, J=18.43, 8.53 Hz, 1H), 2.10 (m, 2H), 2.0-1.8 (m, 3H), 1.69 (s, 3H), 1.62 (s, 3H), 1.7-1.6 (m, 2H), 1.6-1.4 (m, 2H), 1.15 (m, 1H), 1.08 (d, J=6.83 Hz, 3H), 1.00 (d, J=6.49 Hz, 3H); $^{13}$C NMR ($CDCl_3$) (δ): u: 221.6, 131.5, 37.2, 32.3, 25.8, 23.1; d: 124.4, 50.1, 46.8, 34.0, 25.6, 17.6, 13.8; IR (cm$^{-1}$): 2963, 1742, 1456, 1378, 1159; MS (m/z, %): 55 (91), 69 (87), 82 (34), 97 (100), 110 (17), 120 (21), 137 (32), 138 (27), 152 (5), 208 (71); HRMS calcd for $C_{14}H_{24}O$: 208.1827. Found: 208.1833. Anal. calcd for $C_{14}H_{24}O$: C, 80.71; H, 11.61. Found: C, 80.83; H, 11.93. $[α]_D^{17}$=−48.51 (c 1.14, EtOH).

CD Enone 26 from the A-Ring Phenyl Ether 21: A solution of 5 M NaOMe in MeOH (0.14 mL, 0.70 mmol) was added to a solution of ketone 25 (79.6 mg, 0.382 mmol) in 2 mL of MeOH at 0° C. After 10 minutes, a solution of A-ring phenyl ether 21 (109 mg, 0.349 mmol) in 10 mL MeOH was added dropwise. The solution was allowed to stir at ambient temperature for 3 hours and then warmed to reflux for 26 hours. The cooled solution was then partitioned between saturated aqueous $NH_4Cl$ and ether. The organic layer was dried over $Na_2SO_4$ and evaporated. The residue was chromatographed to yield recovered 25 (23.1 mg, 29%), and, after a base-wash (3 M aqueous NaOH, to remove phenol), the CD enone 26 (82.7 mg, 78% based on 25 not recovered ) as a clear oil, TLC $R_f$(20% MTBE/petroleum ether)=0.45. 1H NMR ($CDCl_3$) (δ): 7.01 (d, J=8.19 Hz, 1H), 6.7-6.6 (m, 2H), 5.08 (m, 1H), 3.76 (s, 3H), 2.7-2.5 (m, 3H), 2.5-2.3 (m, 3H), 2.28 (s, 3H), 2.2-2.1 (m, 2H), 2.0-1.8 (m, 3H), 1.69 (s, 3H), 1.61 (s, 3H), 1.6-1.2 (m, 4H), 1.11 (m, 11H), 1.02 (s, 3H), 0.97 (d, J=6.83 Hz, 3H); $^{13}$C NMR ($CDCl_3$)(δ): u: 198.3, 174.3, 157.5, 141.4, 131.3, 130.2, 128.0, 45.1, 36.6, 35.6, 33.6, 32.1, 27.4, 27.0, 26.6, 24.5; d: 130.6, 124.6, 115.4, 110.8, 55.8, 55.1, 33.7, 25.7, 18.7, 18.3, 17.6, 16.4; IR(cm$^{-1}$): 2961, 1661, 1503, 1455, 1251.

The bicyclic enone26 was contaminated with ~10% of its regioisomer 27 that could not be separated by chromatography. This regioisomer was identified by its diagnostic resonance in the $^1$H NMR (δ 0.86, d).

Copper Hydride Reduction. Copper cyanide (220 mg, 2.46 mmol) was suspended in THF (10 mL) and chilled to −20° C. A 2.25 M solution of n-Buli in hexanes (1.1 mL, 2.2 mmol) was added dropwise. The brown solution was stirred at −20° C. for 30 min, and then the temperature was lowered to −50° C. A 1 M solution of Dibal in hexanes (4.9 mL, 4.9 mmol) was added slowly dropwise. The dark brown solution was allowed to stir at −50° C. for 1 h before the CD enone 26 (99.0 mg, 0.242 mmol) was added as a solution in 1:1 THF/HMPA (3.6 mL). The temperature was raised to −20° C. over the next 10 min and then the mixture was allowed to stir at −20° C. for 1 h. The reaction was quenched with a solution of 1:1 saturated aqueous $NH_4Cl$ and 3 M aqueous HCl (20 mL) at −20° C. and allowed to warm to ambient temperature over 30 min. The mixture was filtered and extracted with MTBE. The organic layer was evaporated and then partitioned between MTBE and, sequentially, 1 M aqueous HCl, water, and brine. The organic layer was dried ($Na_2SO_4$), filtered through silica gel, and evaporated to yield the crude reduction product (105 mg) as a pale-yellow oil.

A 0.1 M solution of the Dess-Martin periodinane in $CH_2Cl_2$ (1 mL, 0.1 mmol) was added to a solution of the crude oil from reduction in $CH_2Cl_2$. After 30 min, and again after 1 h, additional portions (1 mL each) of periodinane were added. After 2 h, the reaction was complete (TLC). A solution of 1:1 10% aqueous $Na_2S_2O_4$/1 M aqueous NaOH (20 mL) was added and the mixture was allowed to stir for 30 min. The mixture was then partitioned between MTBE and, sequentially, water and brine. The organic layer was dried ($Na_2SO_4$), filtered through silica, and evaporated to yield the crude oxidation product (104 mg) as a yellow oil.

The crude oil from oxidation was dissolved in a 1:1:4 solution of 1% aqueous KOH/MeOH/THF (20 mL) and stirred at ambient temperature for 1 h. The mixture was partitioned between MTBE and saturated aqueous $NH_4Cl$. The organic layer was evaporated and then partitioned between MTBE and, sequentially, water and brine. The organic layer was evaporated and chromatographed to yield the recovered enone 26 (50.7 mg, 51%) and the trans-hydrindanone 32 (26.1 mg, 52% based on 26 not recovered) as a clear oil, TLC $R_f$(10% MTBE/petroleum ether)=0.42. 1H NMR ($CDCl_3$) (δ): 7.03 (d, J=8.53 Hz, 1H), 6.72 (d, J=2.73 Hz, 1H), 6.64 (dd, J=8.53, 2.73 Hz, 1H), 5.08 (m, 1H), 3.77 (s, 3H), 2.70 (m, 1H), 2.6-2.2 (m, 4H), 2.27 (s, 3H), 2.17 (m, 1H), 2.00 (m, 2H), 1.9-1.5 (m, 6H), 1.69 (s, 3H), 1.5-1.0 (m, 6H), 0.98 (s, 3H), 0.95 (d, J=6.49 Hz, 3H); $^{13}$C NMR ($CDCl_3$) (δ): u: 213.0, 157.7, 142.3, 131.2, 128.1, 42.8, 38.5, 38.3, 35.7, 31.2, 29.0, 27.7, 25.1, 24.6; d: 130.8, 124.9, 114.5, 110.8, 55.22, 55.21, 55.0, 50.4, 35.4, 25.7, 18.4, 18.3, 17.6, 11.5; IR (cm$^{-1}$): 2952, 2869, 1708, 1500, 1251.

Also isolated was a diene (11.0 mg, 11%), presumably formed from elimination of the 1,2 reduction product, as a pale-yellow oil, TLC $R_f$(10% MTBE/petroleum ether)=0.73. $^1$H NMR ($CDCl_3$) (δ): 7.04 (d, J=8.53 Hz, 1H), 6.70 (d, J=2.73 Hz, 1H), 6.65 (dd, J=8.53, 2.73 Hz, 1H), 5.51 (m, 2H), 5.12 (m, 1H), 3.78 (s, 3H), 2.7 (m, 2H), 2.5-1.8 (m, 9H), 2.25 (s, 3H), 1.69 (s, 3H), 1.62 (s, 3H), 1.6 (m, 1H), 1.44 (m, 2H), 1.1 (m, 1H), 0.98 (d, J=6.14, 3H), 0.88 (s, 3H); $^{13}$C NMR ($CDCl_3$) (δ): U: 157.8, 148.7, 142.1, 133.0, 131.1, 127.9, 45.8, 36.4, 36.1, 35.6, 33.6, 33.1, 24.6, 23.9; d: 130.7, 125.1, 124.4, 119.1, 114.7, 110.8, 56.9, 55.2, 33.8, 25.7, 18.8, 18.4, 17.6, 15.5; IR (cm$^{-1}$): 2926, 1609, 1503, 1250, 1046.

Astrogorgiadiol Methyl Ether (36): A sample of 5% Pd/C (20 mg) was added to a solution of the trans-hydrindanone 32 (38.3 mg, 0.0933 mmol) in ethanol (10 mL). Three times in succession, the flask was evacuated and refilled with $H_2$. After 2 h at ambient temperature and pressure, the mixture was filtered and evaporated. Column chromatography afforded the saturated trans-hydrindanone (32.4 mg, 84%) as a clear oil, TLC $R_f$(10% MTBE/petroleum ether)=0.42. $^1$H NMR ($CDCl_3$) (δ): 7.03 (d, J=8.53 Hz, 1H), 6.72 (d, J=2.73 Hz, 1H), 6.64 (dd, J=8.53, 2.73 Hz, 1H), 3.77 (s, 3H), 2.7 (m, 1H), 2.6-2.2 (m, 4H), 2.27 (s, 3H), 2.17 (m, 1H), 1.97 (m, 1H), 1.9-0.8 (m, 16H), 0.98 (s, 3H), 0.93 (d, J=6.49 Hz, 3H), 0.87 (d, J=6.49, 3H), 0.867 (d, J=6.49 Hz, 3H); $^{13}$C NMR ($CDCl_3$) (δ): u: 213.0, 157.7, 142.3, 128.1, 42.8, 39.4, 38.5, 38.3, 35.8, 31.2, 29.0, 27.7, 25.1, 23.7; d: 130.8, 114.5, 110.8, 55.22, 55.20, 55.0, 50.4, 35.6, 28.0, 22.8, 22.5, 18.5, 18.3, 11.5.

A 1.0 M solution of L-Selectride in THF (160 µL, 0.16 mmol) was added dropwise to a solution of the trans-hydrindanone (32.4 mg, 0.0785 mmol) in THF (2 mL) at −78° C. After 2 h, the starting material was 90% consumed (TLC). Additional L-Selectride (80 μL, 0.080 mmol) was added. After an additional 1 h at −78° C., the mixture was quenched with acetone (400 μL) and allowed to warm to ambient temperature. The solution was partitioned between $CH_2Cl_2$ and saturated aqueous $NH_4Cl$. The organic layer was dried ($Na_2SO_4$) and evaporated. The residue was chromatographed to yield astrogorgiadiol methyl ether 36 (17.8 mg, 47% from 32) as a clear oil, TLC $R_f$(20% MTBE/petroleum ether)=0.47. $^1H$ NMR ($CDCl_3$) (δ): 7.04 (d, J=8.19 Hz, 1H), 6.72 (d, J=2.73 Hz, 1H), 6.65 (dd, J=8.19, 2.73 Hz, 1H), 4.04 (bs, 1H), 3.77 (s, 3H), 2.7 (m, 1H), 2.4 (m, 1H), 2.24 (s, 3H), 1.9-0.9 (m, 22H), 0.92 (d, J=6.49, 3H), 0.863 (d, J=6.49 Hz, 3H), 0.858 (d, J=6.49 Hz, 3H); $^{13}C$ NMR ($CDCl_3$) (δ): u: 157.8, 142.5, 127.9, 42.9, 39.5, 36.1, 34.1, 31.1, 30.3, 30.1, 27.7, 24.4, 23.7; d: 130.8, 114.5, 110.7, 67.2, 56.2, 55.2, 47.7, 40.9, 35.7, 28.0, 22.8, 22.5, 18.7, 18.4, 11.0; IR ($cm^{-1}$): 3453 (br), 2932, 2867, 1499, 1251. HRMS calcd for $C_{28}H_{46}O_2$: 414.3500. Found: 414.3487.

Astrogorgiadiol (3): The aryl methyl ether 36 (7.7 mg, 18.6 mmol) was dissolved in $CH_2Cl_2$ (1 mL). Triethylsilane (60 μL, 376 mmol) and a 21 mM solution of tris(pentafluorophenyl) boron (100 μL, 1.95 mmol) in $CH_2Cl_2$ were added. After 1 h, the reaction was quenched with triethylamine (200 μL). The solution was filtered through silica and evaporated. The residual oil was diluted with 1 M tetrabutylammonium fluoride (1 mL) in THF. After 24 h, the solvent was removed in vacuo and the residual oil was partitioned between water and ether. The organic layer was evaporated and chromatographed to yield 3 (6.3 mg, 85% yield) as a clear oil, TLC $R_f$(30% MTBE/petroleum ether) =0.23, $[a]_D^{18}$=−7.4 (c 0.095, $CHCl_3$). $^1H$ NMR ($C_6D_6$) d 6.93 (d, J=8.19 Hz, 1H), 6.60 (d, J=2.73 Hz, 1H), 6.45 (dd, J=8.19, 2.73 Hz, 1H), 4.09 (bs, 1H), 3.8 (m, 1H), 2.7 (m, 1H), 2.3 (m, 1H), 2.22 (s, 3H), 1.9-0.8 (m, 22H), 0.98 (d, J=6.49 Hz, 3H), 0.925 (d, J=6.49 Hz, 3H), 0.923 (d, J=6.49 Hz, 3H), 0.59 (s, 3H); $^{13}C$ NMR ($CDCl_3$) d u: 155.2, 143.3, 43.4, 40.3, 37.0, 34.8, 31.6, 31.3, 31.0, 28.5, 25.1, 24.7; d: 131.7, 116.4, 113.2, 67.2, 56.8, 48.1, 41.6, 36.5, 28.8, 23.4, 23.1, 19.3, 11.6, 0.4; IR ($cm^{-1}$): 3387 (br), 2932, 2869, 1463. The $^1H$ NMR spectrum of this substance was superimposable on those provided.

Scheme 1

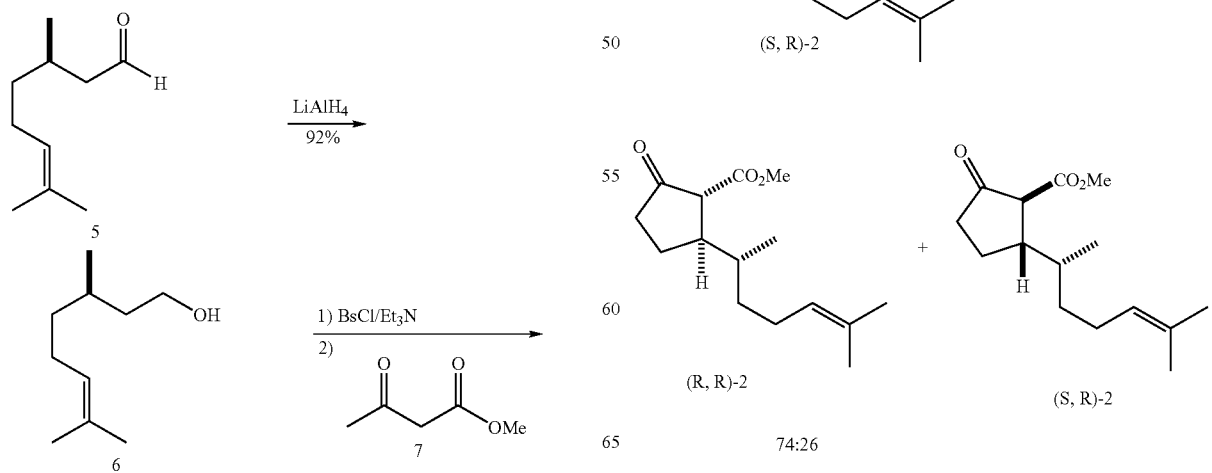

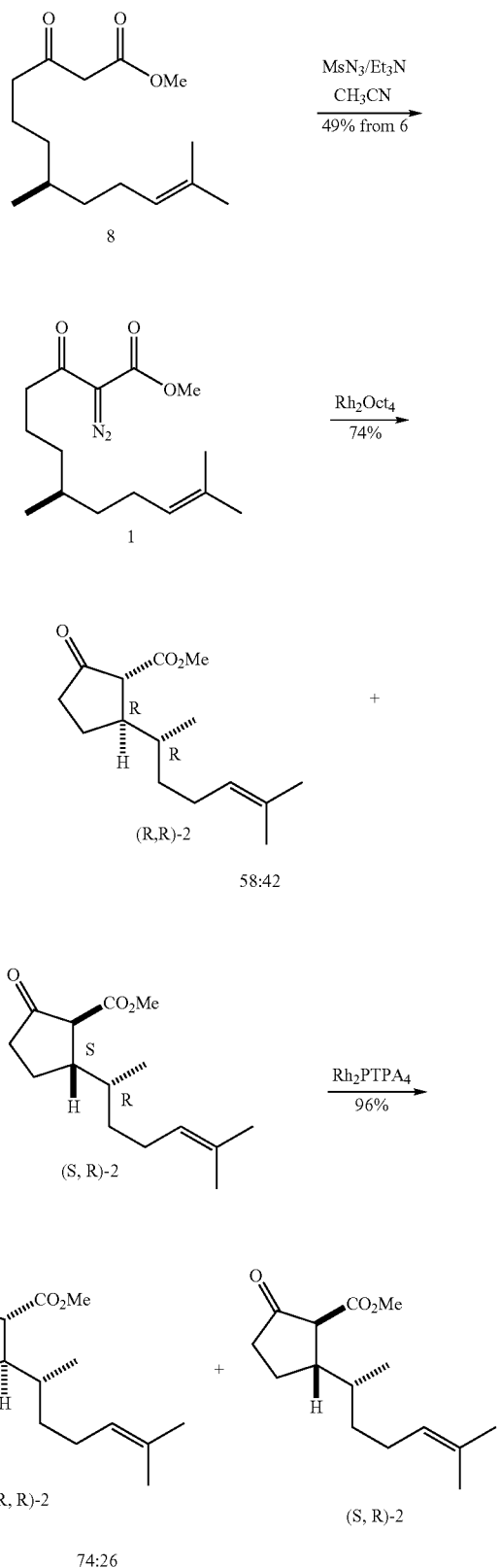

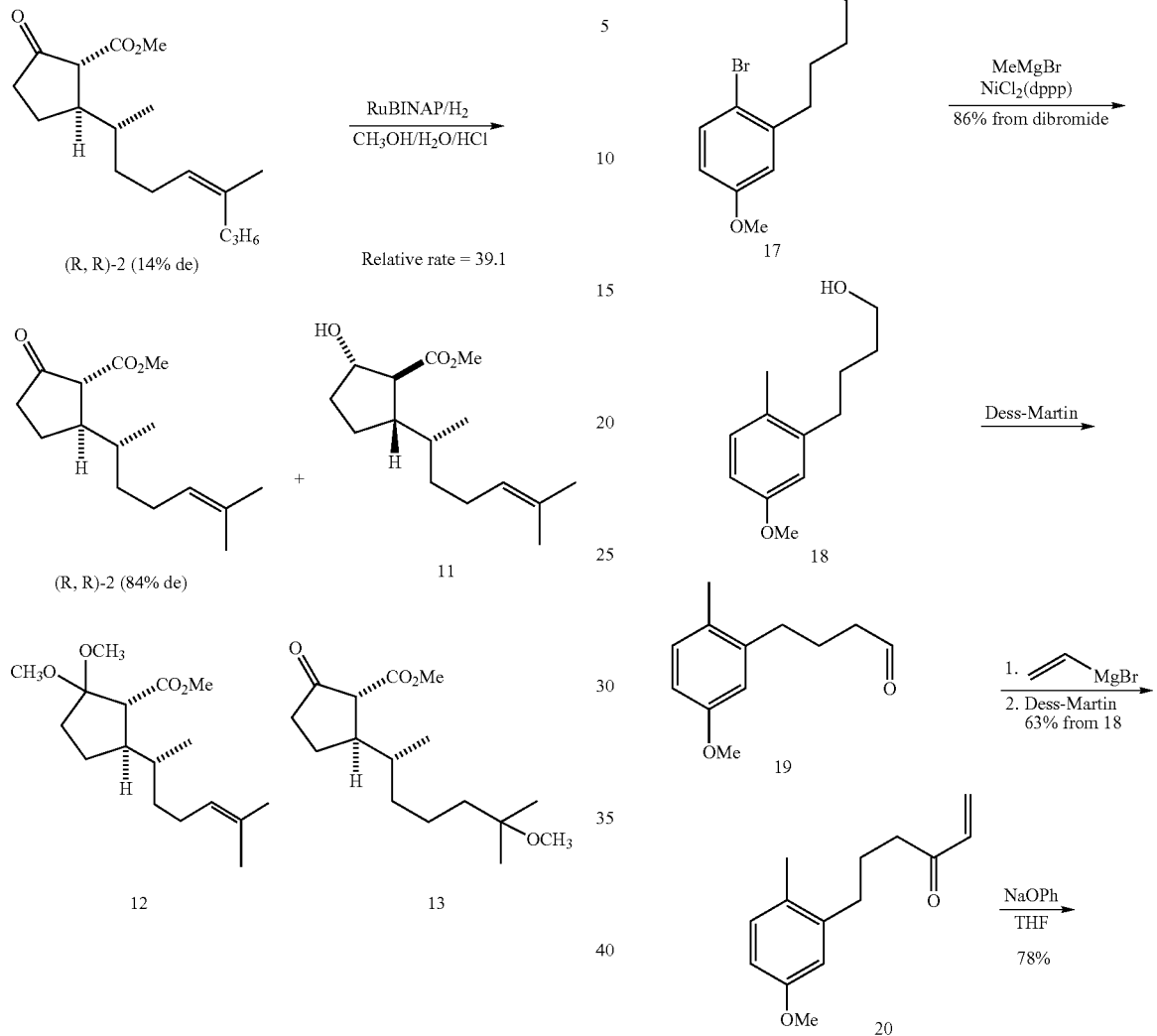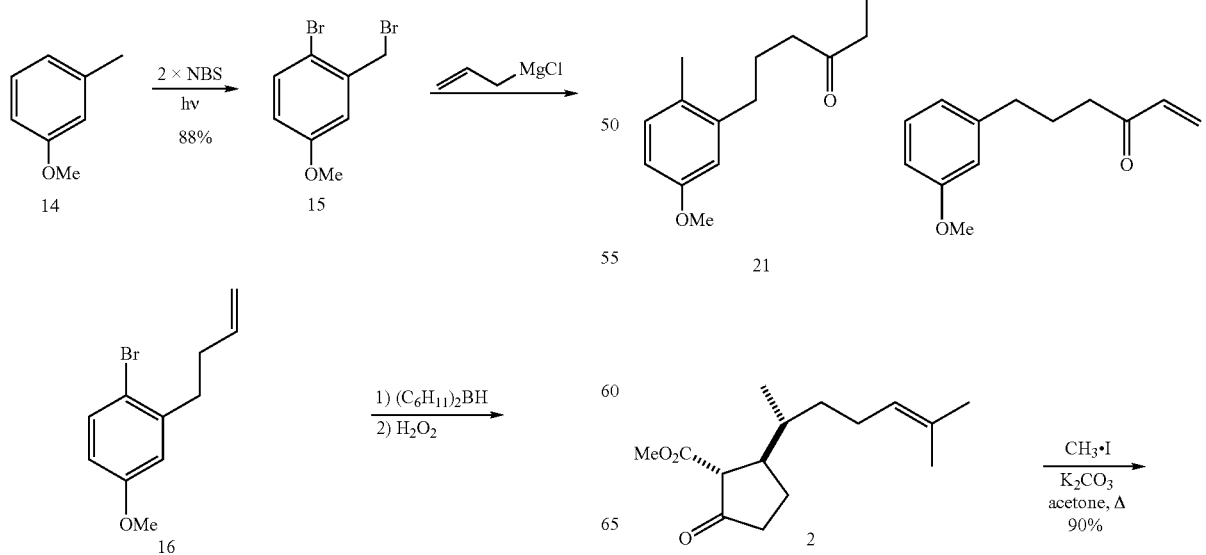

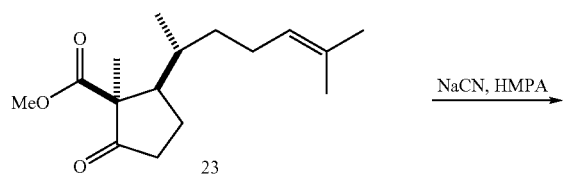
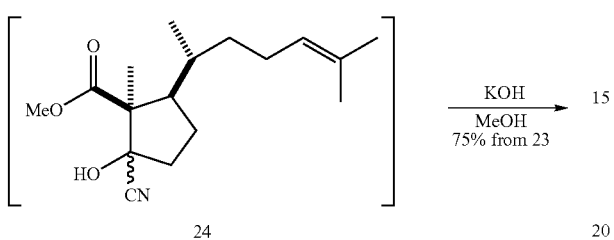
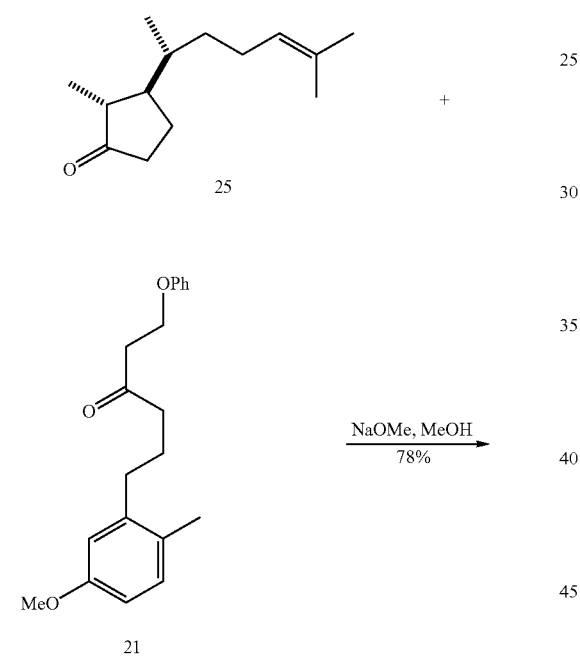
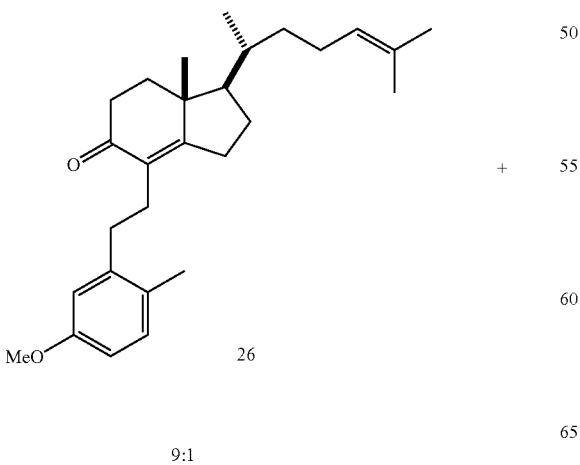
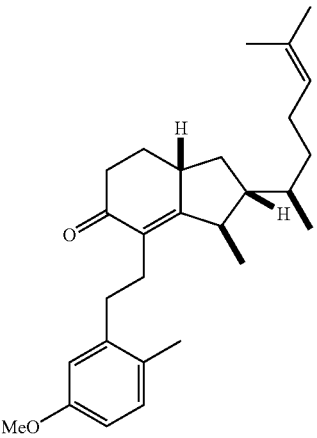
Scheme 5
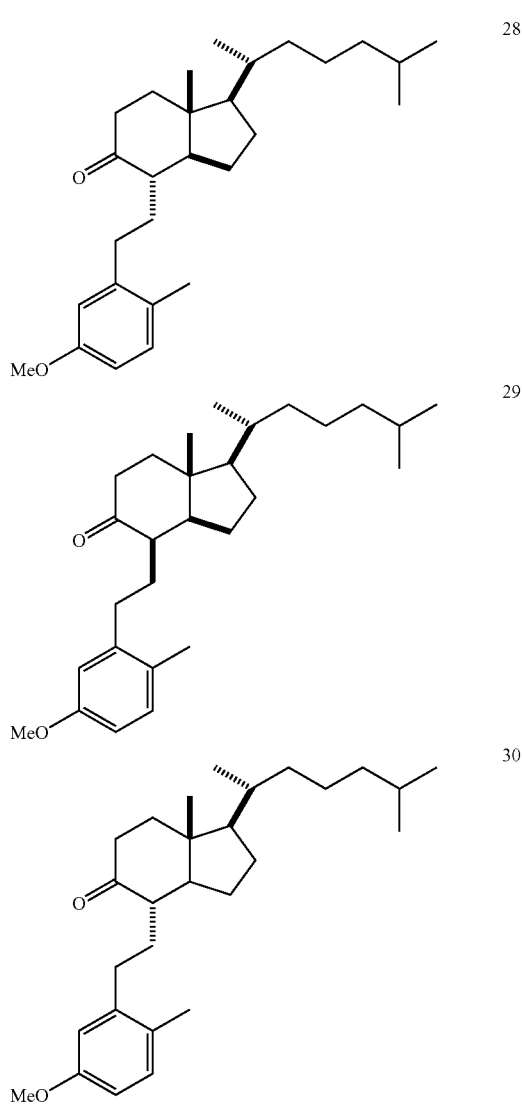

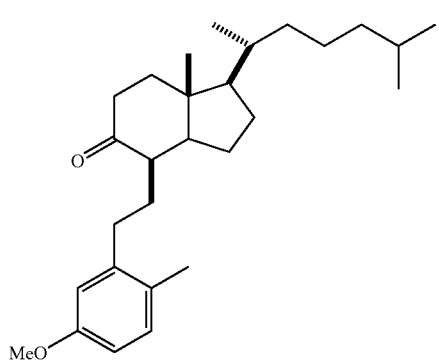
31
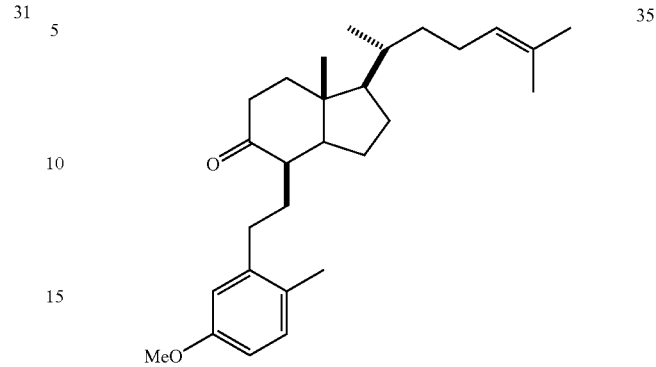
35
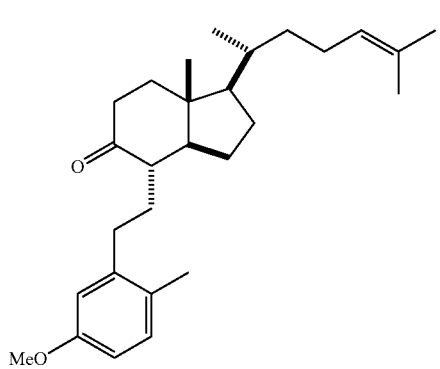
32
Scheme 6
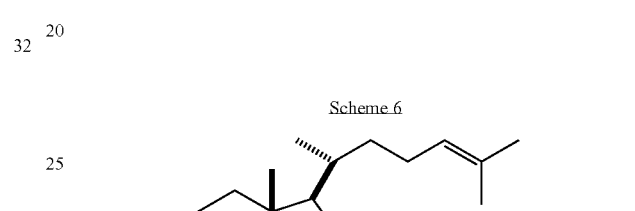
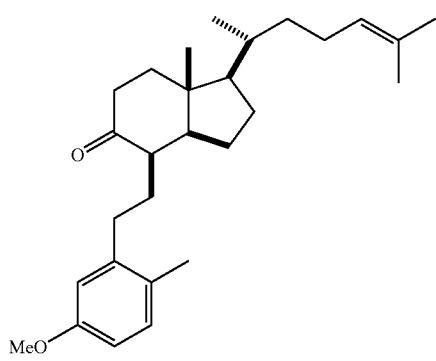
33
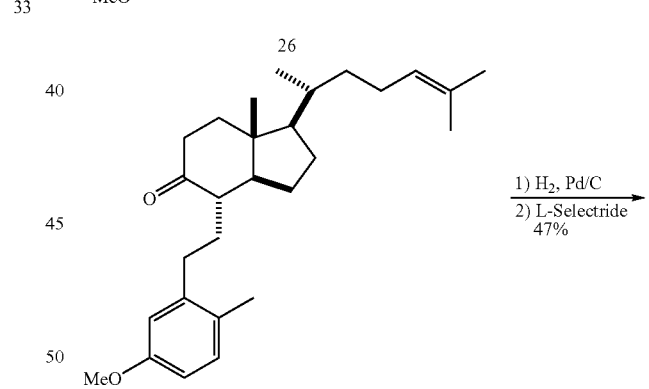
26
1) H₂, Pd/C
2) L-Selectride
47%
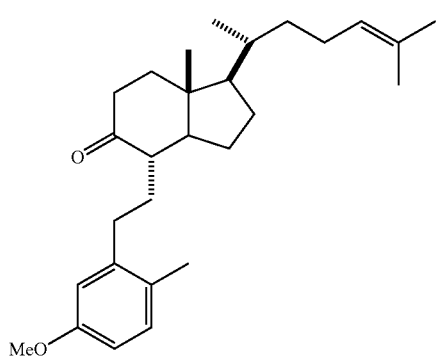
34
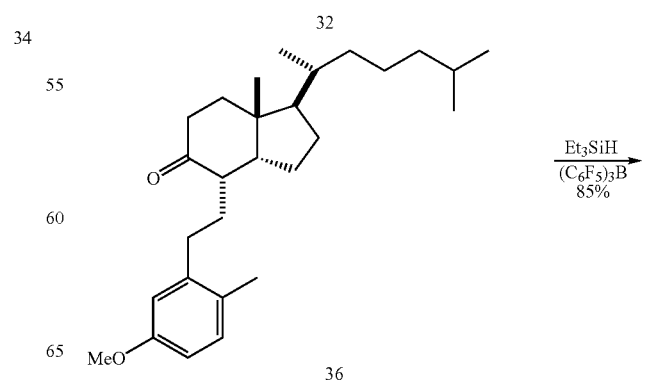
32
Et₃SiH
(C₆F₅)₃B
85%
36

-continued

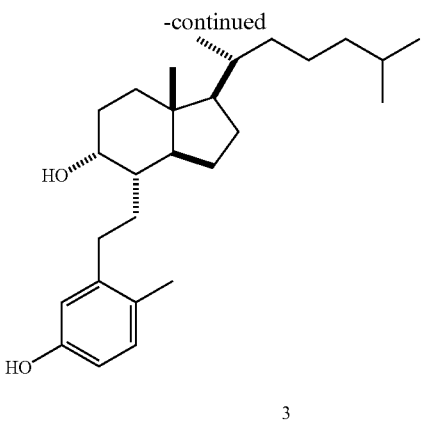

3

Example 2

Gene Expression Changes Induced by Astrogorgiadiol

Changes in levels of mRNA encoding osteopontin induced by astrogorgiadiol were studied by Northern blot. Northern blot analysis was performed as described in Farach-Carson American Journal of Physiology 265: F705-F711 (1993), modified to include varying concentrations of astrogorgiadiol.

Briefly, ROS 17/288 cells were treated with 1 nM 1, 25 (OH)$_2$vitD$_3$ (BIOMOL Research Laboratories Inc., Plymouth Meeting, Pa.) or 1 nM 1, 25 (OH)$_2$ vitD$_3$ and 3 nM, 30 nM or 300 nM astrogorgiadiol for 0, 3 or 24 hours prior to harvest or with 3 nM, 30 nM or 300 nM astrogorgiadiol. mRNA was extracted using standard techniques. Osteopontin mRNA was detected using a $^{32}$P-labeled osteopontin cDNA probe.

As shown in FIG. 1, the Northern blot showed increased osteopontin mRNA in response to induction by 1,25 (OH)$_2$ vitD$_3$. The presence of astrogorgiadiol downregulated osteopontin mRNA in a dose-dependent manner. 3 nM astrogorgiadiol decreased 1,25 (OH)$_2$ vitD$_3$-induced osteopontin mRNA to levels approaching control levels. The presence of 30 nM or 300 nM astrogorgiadiol decreased the level of osteopontin mRNA below control levels.

We claim:

1. A method of downregulating mRNA encoding osteopontin comprising administering to a mammalian cell or a mammal an amount of astrogorgiadiol effective to downregulate production of mRNA encoding osteopontin.

2. A method of reducing production of osteopontin comprising administering to a mammalian cell or a mammal an amount of astrogorgiadiol effective to reduce production of osteopontin in said cell or mammal.

3. A method of treating osteoporosis comprising administering to a patient in need of such treatment a therapeutically effective amount of astrogorgiadiol.

4. A method of treating systemic lupus erythematosis comprising administering to a patient in need of such treatment a therapeutically effective amount of astrogorgiadiol.

5. A method of treating multiple sclerosis comprising administering to a patient in need of such treatment a therapeutically effective amount of astrogorgiadiol.

6. The method of claim 3 further comprising administering an additional compound useful for treatment of osteoporosis in conjunction with astrogorgiadiol to the patient.

7. A pharmaceutical composition comprising astrogorgiadiol and a pharmaceutically acceptable solid carrier or aqueous diluent.

8. The method of claim 1 wherein said astrogorgiadiol is administered to a mammalian cell.

9. The method of claim 2 wherein said astrogorgiadiol is administered to a mammalian cell.

10. The method of claim 4 further comprising administering an additional compound useful for treatment of systemic lupus erythematosis in conjunction with astrogorgiadiol to the patient.

11. The method of claim 5 further comprising administering an additional compound useful for treatment of multiple sclerosis in conjunction with astrogorgiadiol to the patent.

* * * * *